United States Patent [19]

Zaiger et al.

[11] Patent Number: Plant 7,751

[45] Date of Patent: Dec. 17, 1991

[54] PEACH TREE "EVA'S PRIDE"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95351

[21] Appl. No.: 605,671

[22] Filed: Oct. 29, 1990

[51] Int. Cl.[5] ..... A01H 5/00

[52] U.S. Cl. ..... Plt./43

[58] Field of Search ..... Plt./40–43

*Primary Examiner*—James R. Feyrer

[57] ABSTRACT

A new and distinct variety of peach tree with the following unique combination of desirable features:

1. Low winter chilling requirement of approximately 250 hours.
2. Heavy and regular production of fruit.
3. Producing large, firm, yellow flesh fruit.
4. Fruit with good storage and shipping quality.
5. Fruit having good flavor and eating quality.
6. Vigorous, semi-upright growth.

1 Drawing Sheet

ORIGIN OF THE VARIETY

The present new variety of peach tree was developed by us in the experimental orchards located near Modesto, Calif. as a third generation cross between an open pollinated Red Grand Nectarine (U.S. Plant Pat. No. 1,060) seedling and Desert Gold Peach (non-patented). A large group of these third generation seedlings were grown and maintained under careful observation, during which time we recognized the desirable characteristics described above and selected the variety for asexual reproduction and commercialization.

ASEXUAL REPRODUCTION OF THE VARIETY

Asexual propagation of the new and distinct variety of peach tree was preformed by budding in the experimental orchard located near Modesto, Calif., shows that said characteristics run true to the original tree and are identical in all respects.

SUMMARY OF THE VARIETY

The herein variety of peach tree is of large size, vigorous, semi-upright in growth and a regular and productive bearer of large size, yellow flesh, clingstone fruit ripening in mid June. The fruit is further characterized by relatively uniform ripening throughout the tree, holding firm on the tree for 5–6 days after picking ripe, having good flavor and eating quality with the ability to ship to long distance markets. In comparison to its low chilling parent, Desert Gold Peach (non-patented), the fruit is larger in size, has firmer flesh with greater shipping quality, ripens more uniformly and matures approximately two weeks later.

PHOTOGRAPHS OF THE VARIETY

The accompanying photographic illustrations show typical specimens of the foliage and fruit of our new peach variety, the upper and lower surface of the leaves being shown, with fruit specimens showing the exterior and a sectional view of the fruit divided in the suture plane to reveal flesh coloration and showing a stone remaining in place. The illustrations were taken shortly after being picked at maturity (firm ripe) and the colors are as nearly true as reasonably possible in color representation of this type.

DESCRIPTION OF THE VARIETY

The following is a detailed botanical description of the new and distinct variety of peach tree, its flowers, foliage and fruit, as based on observations of specimens grown at Modesto, Calif., with color terminology (except those in common color terms) in accordance with Reinhold Color Atlas by A. Kornerup and J. H. Wanscher.

Tree:
- *Size.*—Large.
- *Vigor.*—Vigorous.
- *Form.*—Semi-upright, normally pruned to vase shape.
- *Production.*—Productive.
- *Bearer.*—Regular.
- *Density.*—Medium dense.

Trunk:
- *Size.*—Medium to stocky.
- *Texture.*—Medium shaggy.
- *Color.*—Brown to grayish brown.

Branches:
- *Size.*—Medium.
- *Texture.*—Medium rough.
- *Lenticels.*—Numerous. Medium size.
- *Color.*—Light brown to brown.

Leaves:
- *Size.*—Large. Average length — 6½". Average width — 1⅝".
- *Texture.*—Smooth.
- *Margin.*—Crenate.
- *Petiole.*—Medium length. Medium thickness.
- *Gland.*—Reniform. Medium size. Number varies 1 to 5. Average number 3. Positioned on upper portion of petiole and on base of leaf blade, usually alternate.
- *Color.*—Upper surface — green to dark green (27-F-6) to (27-F-8). Lower surface — light green to dull green (27-E-6) to (27-E-7).

Flower buds:
- *Size.*—Large.
- *Form.*—Round, plump.
- *Pubescence.*—Pubescent.

Flowers:
- *Size.*—Large — showy.

*Blooming period.*—Date of first bloom Feb. 19, 1988. Date of last bloom Feb. 25, 1988. Varies slightly due to weather conditions.

*Pollen.*—Present.

*Color.*—Pink.

Fruit:

*Maturity when described.*—Firm ripe.

*Date of first picking.*—June 16, 1988.

*Date of last picking.*—June 22, 1988.

*Size.*—Large. Average diameter axially — $2\frac{1}{2}''$ to $2\frac{7}{8}''$. Average transversely in suture plane $2\frac{1}{2}''$ to $2\frac{7}{8}''$.

*Form.*—Globose to slightly flattened at stem and apex.

*Suture.*—Shallow — extends from base to apex.

*Cavity.*—Rounded to slightly elongated in suture plane. Average depth — $\frac{1}{2}''$. Average breadth — $\frac{3}{4}''$.

*Apex.*—Retuse.

*Base.*—Retuse.

Skin:

*Thickness.*—Medium.

*Texture.*—Medium.

*Tendency to crack.*—None.

*Down.*—Moderate.

*Color.*—Yellow ground color — (5-A-6) to (5-A-8) overspread with red blush (9-A-7) to (9-A-8).

Flesh:

*Texture.*—Firm.

*Ripens.*—Even.

*Juice.*—Moderate.

*Flavor.*—Good — subacid to mild.

*Eating quality.*—Good.

*Aroma.*—Moderate.

*Color.*—Light yellow to yellow (4-A-6) to (4-A-6), small light red streaks (9-A-7) between apex of fruit and apex of stone in some fruit.

Stone:

*Type.*—Clingstone.

*Size.*—Medium. Average length — $1\frac{1}{4}''$. Average breadth — $1\frac{1}{8}''$. Average thickness — $\frac{5}{8}''$.

*Base.*—Varies from round to straight.

*Apex.*—Varies from round to slight point.

*Surface.*—Irregularly furrowed toward apex. Pitted throughout, heavier toward base.

*Tendency to split.*—Very slight.

*Color.*—Light brown to brown (8-C-6) to (8-D-6).

Use: Dessert.

*Market.*—Local and long distance.

Keeping quality: Good.

Shipping quality: Good.

The new and distinct peach tree, its flowers and fruit herein described may vary in slight detail due to climatic, soil conditions and cultural practices under which the variety may be grown; the present description is that of the variety grown under the ecological conditions prevailing near Modesto, Calif.

We claim:

1. A new and distinct variety of peach tree, substantially as illustrated and described, characterized by its large size, vigorous, semi-upright growth, its low winter chilling requirement of approximately 250 hours and being a regular and productive bearer of large size, yellow flesh, clingstone fruit with good flavor and eating quality; in comparison to its low chilling parent, Desert Gold Peach (non-patented), the fruit is larger in size, has firmer flesh with greater shipping quality, ripens more uniformly, and is approximately two weeks later in maturity.

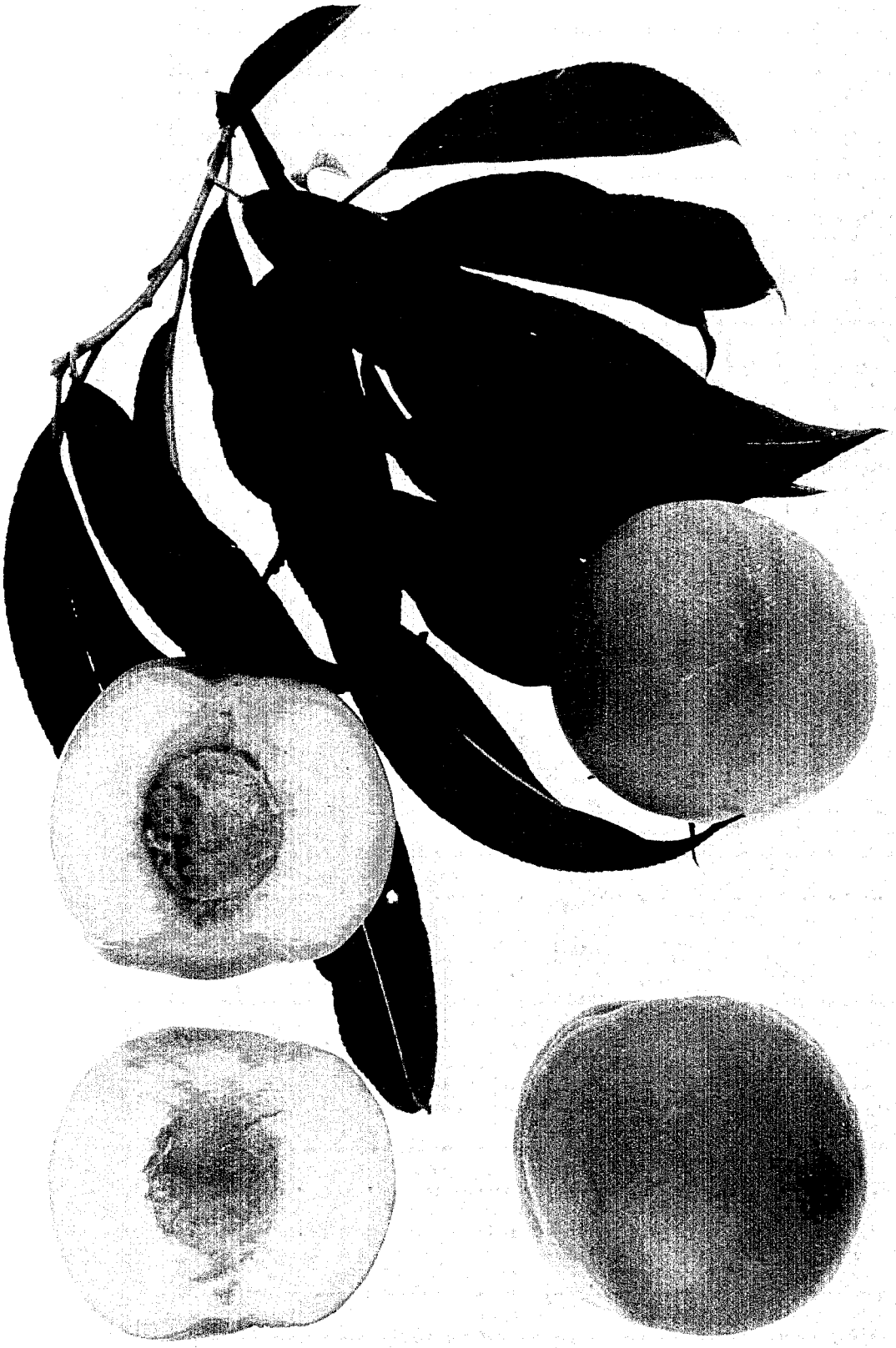

* * * * *